United States Patent [19]

Jones et al.

[11] Patent Number: 4,978,434

[45] Date of Patent: Dec. 18, 1990

[54] APPARATUS AND METHOD FOR MEASURING $SO_2$ USING A ZIRCONIUM OXIDE ANALYZER

[75] Inventors: James E. Jones, Wadsworth, Ohio; Clifford Y. Scott, Park Ridge, N.J.

[73] Assignee: Westinghouse Electric Corp., Pittsburgh, Pa.

[21] Appl. No.: 302,154

[22] Filed: Jan. 26, 1989

[51] Int. Cl.$^5$ .......................................... G01N 27/407
[52] U.S. Cl. ................................ 204/153.1; 73/23.31; 204/153.18; 204/153.19; 204/421; 204/424
[58] Field of Search ........................ 204/1 S, 421–429, 204/153.1, 153.18, 153.19; 73/23

[56] References Cited

U.S. PATENT DOCUMENTS

| | | | |
|---|---|---|---|
| 3,514,377 | 5/1970 | Spacil et al. ......................... | 204/427 |
| 3,805,196 | 4/1974 | Feichtner et al. ..................... | 333/72 |
| 3,928,161 | 12/1975 | McIntyre et al. ..................... | 204/1 S |
| 4,218,297 | 8/1980 | Henault et al. ...................... | 204/424 |
| 4,391,690 | 7/1983 | Lin et al. ........................... | 204/428 |
| 4,394,240 | 7/1983 | Pebler ............................... | 204/1 S |

OTHER PUBLICATIONS

Murphy et al., "Foundations of College Chemistry", 2nd Ed., 1975, pp. 341–352, 605.

Primary Examiner—T. Tung
Attorney, Agent, or Firm—G. E. Hawranko

[57] ABSTRACT

An arrangement for determining an amount of $SO_2$ present in the gaseous emissions of a combustible process utilizes an oxygen measuring device and the resultant $O_2$ measurement to make an inferred determination of such $SO_2$ measurement. A processing element reads an EMF signal representative of the $O_2$ present and calculates therefrom, an amount of $SO_2$ which can be selectively or automatically displayed alone or in conjunction with the $O_2$ measurement.

7 Claims, 2 Drawing Sheets

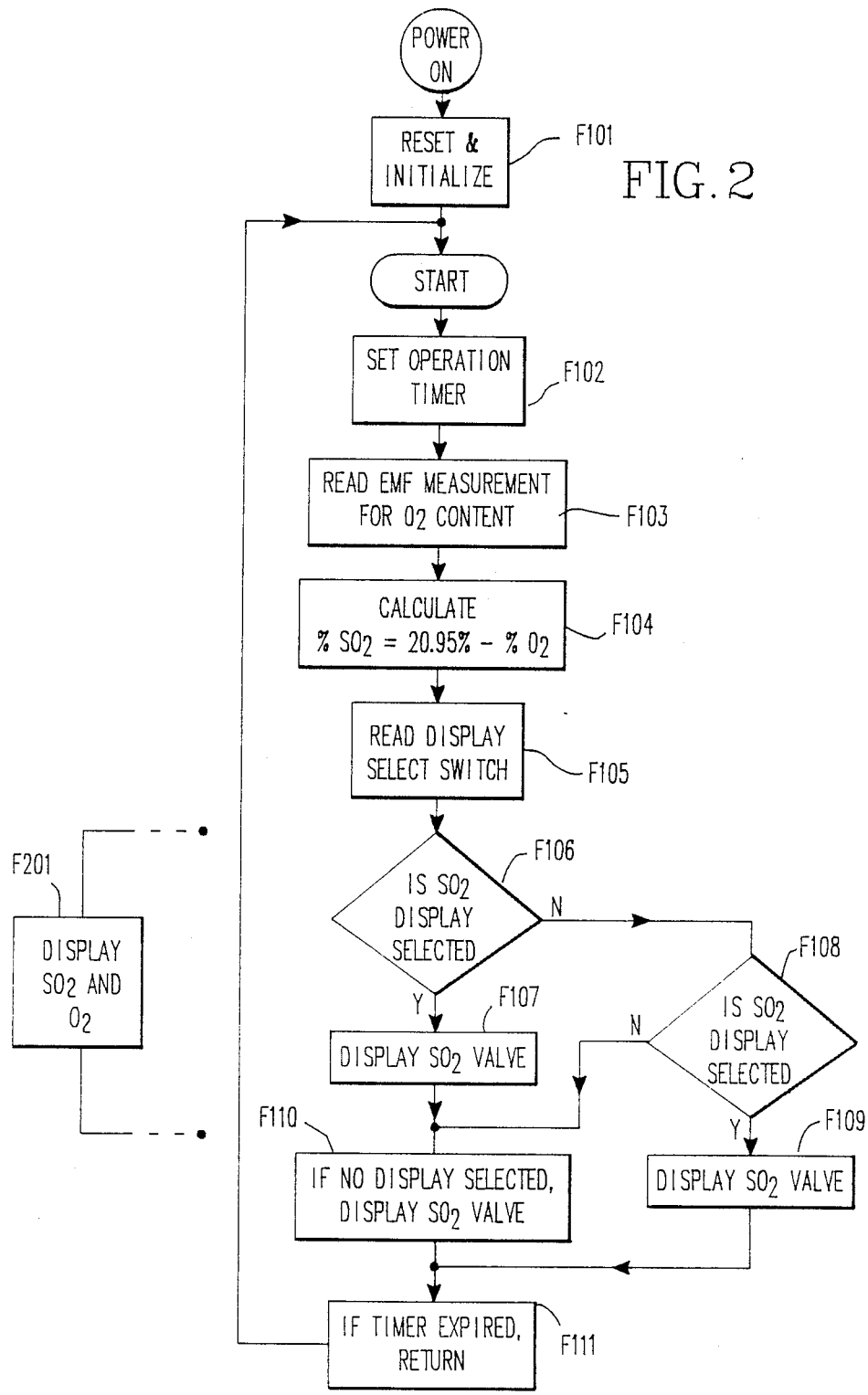

APPARATUS AND METHOD FOR MEASURING SO₂ USING A ZIRCONIUM OXIDE ANALYZER

FIELD OF THE INVENTION

This invention relates to an apparatus for measuring $SO_2$ using a zirconium oxide analyzer and subsequently displaying such measurement. More particularly, this invention relates to such an apparatus as can display an inferred measurement of $SO_2$ based on an actual measurement of oxygen taken from emissions from a sulfur burning process.

BACKGROUND OF THE INVENTION

Sulfur dioxide ($SO_2$) stack emissions have been identified as a contributor to the formation of acid rain and, accordingly, the detection, measurement and control of such emissions are increasingly coming under scrutiny and regulation by various governments. Certain industries particularly are being more closely scrutinized since they are more apt to produce $SO_2$ emissions as a byproduct of the processes they engage in to produce their products. For example electric utilities and industrial power plants are a source of such $SO_2$ emissions due to the fact that they burn fossil fuels. Such carbon based fuels are especially in need of emissions monitoring because of the fact that in addition to $SO_2$, other pollutants are also emitted such as the carbon based pollutants CO and $CO_2$. Certain electric utility companies which utilize high sulfur coal in their coal fired power plants have been forced to install expensive scrubbing equipment and monitoring analyzers to insure compliance with government standards. Additionally, it is essential that such equipment operate continuously and reliably with a minimum of maintenance.

For such monitoring or analysis of multiple pollutant gas stack emissions, it has become necessary to employ costly and complicated equipment to measure for such a variety of constituents and to the precise concentrations required by the various government regulatory agencies. One example of such a measurement or analyzing device used for the measurement of gas constituents in combustible environment is a spectrophotometric device which would utilize either ultraviolet or infrared light to determine the amount of $SO_2$ present by the amount of radiation absorbed at particular wavelengths specifically associated with $SO_2$. Additionally, the use of such spectrophotometric devices can be made either with a gas sample or with an in situ sensor which looks across the gas stack or through a short path length enclosed within a stack mounted probe. An example of an analyzing device using spectrographic techniques for the measurement or detection of various gaseous constituents is found in U.S. Pat. No. 3,805,196 which issued to Mr. J. D. Feichtner et al. on Apr. 16, 1974 and discloses the use of an acousto-optic tunable filter (AOTF). Depending on the geometry of the crystal from which the AOTF is manufactured and the RF signal that is used for modulation, the AOTF can be effective for detecting the absorption characteristics of specific gases through which an ultraviolet or infrared light beam is directed. Though this approach has proven very effective, it should be realized that to incorporate this approach into a workable arrangement requires additional detecting and support devices and can consequently become somewhat costly.

Still another approach to measuring $SO_2$ can be found in U.S. Pat. No. 4,391,690 which issued to Mr. C. Y. Lin et al. on July 5, 1983. In this patent, a solid electrolyte electrochemical cell device specifically associated with $SO_2$, provides an EMF signal based on the Nernst equation which indicates the $SO_2$ content of the gas being monitored. With this device, an adjustment is necessary to eliminate the effect of oxygen on the EMF measurement signal. Although this approach is also effective, it would be advantageous if a device were available that could produce a measurement of $SO_2$ in conjunction with some other function that such a device could perform.

An example of such a multipurpose measuring arrangement can be found in U.S. Pat. No. 4,394,240 issued to Mr. A. R. Pebler on July 19, 1983. Here, a combined sulfur oxide/oxygen measuring apparatus is provided wherein oxygen ion and oxy-anion conductive solid electrolyte electrochemical cells are combined to form a single gas measuring apparatus. An even more advantageous device than one which uses a combination of solid electrolyte cells would be one that could provide more than one reading using only one solid electrolyte cell.

Single purpose probes having a single solid electrolyte cell have been employed to measure oxygen in the gas stream of a combustible environment in such a manner that the oxygen analyzer is protected from damage that may occur from the contact of that analyzer with particulate matter such as fly ash, cinder, etc. An example of such a probe can be found in U.S. Pat. No. 3,928,161 which issued to Mr. W. H. McIntyre et al. on Dec. 23, 1975. This patent is assigned to the same assignee as the present invention and is hereby incorporated by reference to illustrate the use a solid electrolyte material as an oxygen analyzer, such material being, for instance, a composition of zirconia and oxides of calcium or related material which provides sufficient oxygen ion conduction.

An example of an industrial process where such an $SO_2$ determining arrangement would be beneficial is in the area of a paper processing plant where sulfur burners are utilized, such sulfur burners which generate therefrom, high concentrations of $SO_2$ as well as quantities of sulfuric acid which are used in the paper processing operation. Though the previous discussion has dealt with the measurement of $SO_2$ from the standpoint of an emissions control operation, it should be realized that $SO_2$ may be necessary for industrial operations such as chemical processing or paper mill operations for instance, and that accordingly, such measurement of $SO_2$ is utilized as an operating guide or a closed loop control on a process control system where there are no emissions to air involved.

SUMMARY OF THE INVENTION

It is therefore an object of this invention to provide an arrangement for determining and indicating an amount of $SO_2$ using a zirconium oxide probe constructed solely as an oxygen analyzer.

In accordance with the principles of the present invention, there is provided an arrangement for determining an amount of $SO_2$ present in a sulfur burning combustible process which includes a means for measuring an amount of oxygen present in the gaseous emissions resulting from such combustible process, and a means for calculating such amount of $SO_2$ as a function of such oxygen measurement, the calculating means determining such amount of $SO_2$ based on such sulfur burning combustible process having as the essential gaseous emissions, only the elements of air and such amount of $SO_2$.

BRIEF DESCRIPTION OF THE DRAWINGS

FIG. 2 is a program flow chart suitable for embodying the operation of the calculation of the amount of $SO_2$ based on the measured amount of $O_2$.

DESCRIPTION AND OPERATION

Figure 1:
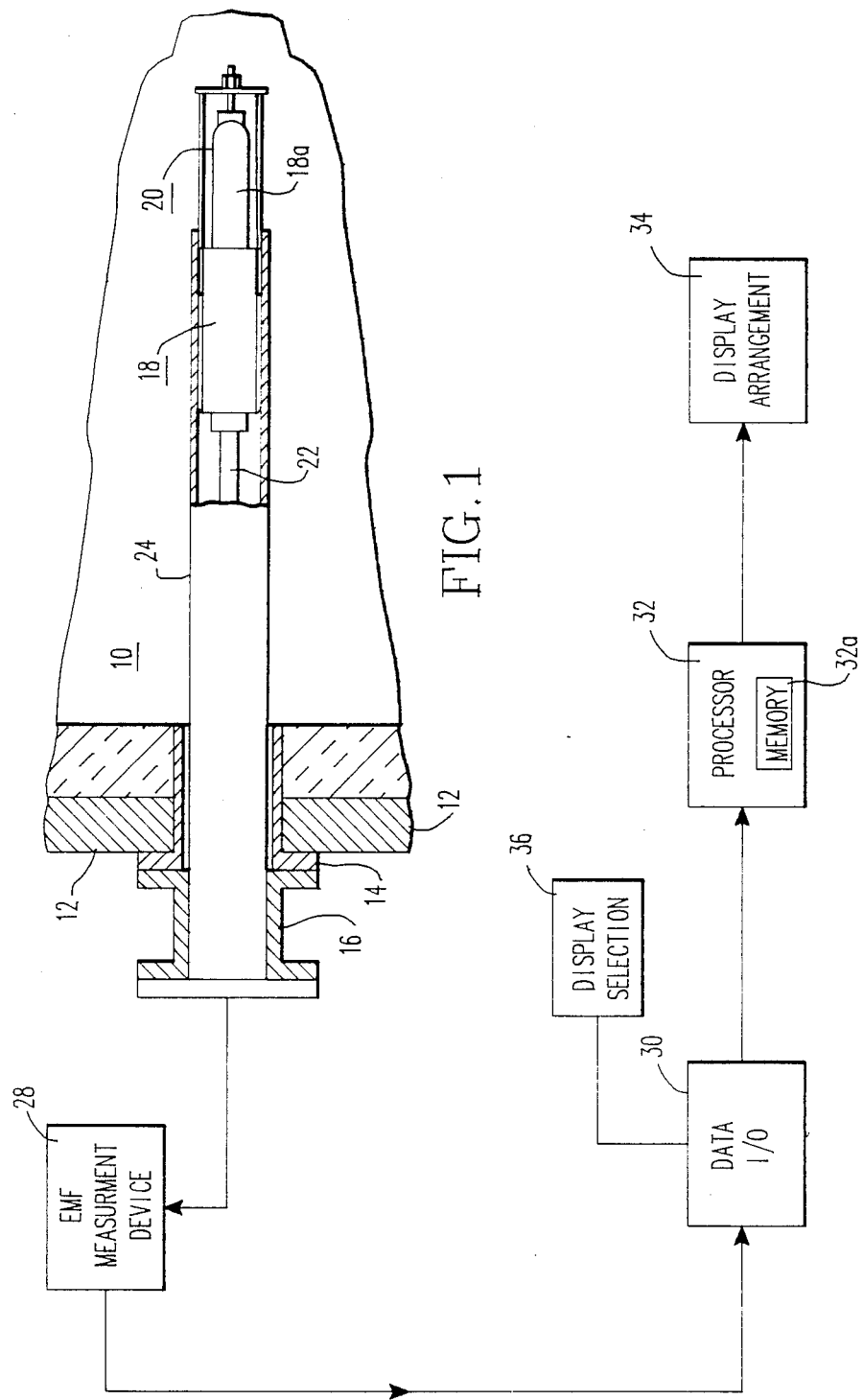
FIG. 1 is an elevational view partly in block diagram form of an $SO_2$ determining arrangement constructed in accordance with the principles of the present invention.

As seen in FIG. 1, an arrangement for determining a measure of $SO_2$ generated in a sulfur burning combustible process utilizes a solid electrolyte oxygen probe assembly 10. The oxygen probe assembly 10 is inserted through the outside wall 12 of a gas stack so as to monitor the oxygen content of the gas emissions from the combustible process, such operation being commonly utilized in the industry as a means of determining the fuel burning efficiency of a combustible process. The oxygen probe assembly 10 is secured to the wall 12 of the gas stack in a conventional manner utilizing for instance, a flange arrangement 14, 16 whereby a furnace flange 14 and a probe flange 16 are arranged in a manner to provide a secure fit of the oxygen probe assembly 10 to the gas stack wall 12.

The oxygen probe assembly 10 includes a solid electrolyte oxygen sensor assembly 18 in which is disposed the solid electrolyte oxygen sensor cell 18a. Installed over the oxygen sensor assembly 18 is a protective shield 20 constructed of a suitable porous material so as to allow exposure of the gas emissions to the solid electrolyte oxygen sensor assembly 18. The solid electrolyte oxygen sensor assembly 18 also includes an extender member 22 which is utilized for positioning the solid electrolyte oxygen sensor assembly 18 within the gas stack. A tubular support member 24 is also provided as the means for providing stationary support to the solid electrolyte sensor assembly 18.

An EMF value developed by the solid electrolyte sensor cell 18a is communicated externally of the gas stack over signal line 26 to an EMF measurement device 28, such EMF value being representative of an amount of $O_2$ which is in excess of the stochiometic amount associated with the process. The EMF measurement device 28 is effective for providing an EMF signal which is compatible with the data I/O device 30 associated with the processor element 32. The data I/O device 30 can be an A/D converter or some similar device which provides a digital signal equivalent of an input signal so as to be capable of being read by the processor element 32. Such an A/D converter can be of a commercially available type such as for example, an ADC0844 manufactured by the National Semiconductor Corp.

The processor device 32 can also be provided as a standard commercially available device such as for example, an 8-bit CMOS microprocessor designated as an 80C51 available in commercial quantities from the Intel Corp. This processor device 32 includes a CPU, associated ROM and RAM memory, I/O ports, an on-chip oscillator and the necessary control circuitry. The processor device 32 can be programmed to perform the necessary calculations and display operations in accordance with the features of the present invention, such programming to be described in further detail with reference to FIG. 2.

Once such calculations have been performed by the processor device 32, the necessary information is available for display on the display arrangement 34 which can be of any commercially available type including a four character alpha-numeric LCD display or the like which are readily available in commercial quantities from manufacturers such as Siemens and National Semiconductor. Additionally, the display arrangement could be comprised of an analog type metering device which could include an indicating needle movable over a series of calibrated lines in response to an appropriate input such as an EMF value. It should be appreciated that for this arrangement, the operation of performing a specific calculation can be avoided by merely calibrating the deflection of the indicating needle of the analog meter such that the specific EMF value representing the $O_2$ measurement and which correlates with the $SO_2$ measurement, could be directly translated. Also associated with the display arrangement 34 is arrangement 36 for selecting which value to display, the $O_2$ or the $SO_2$ measurement; such selecting arrangement being for instance a manually operated switch. It should be understood that such a selection device is merely an option for making the $SO_2$ determining arrangement of the present invention more commercially attractive and can be substituted for by an automatically cycling display arrangement which would require no manual input.

The operation of the $SO_2$ determining arrangement of the present invention will be more readily understood when read in conjunction with the operational flow chart set forth in FIG. 2. Following powering up of the $SO_2$ determining arrangement illustrated in FIG. 1, the processor device 32 executes the appropriate resetting and initialization operations which include but are not limited to initializing associated ports and registers, this initializing and resetting operation being shown as function block F101.

After initialization, the program loop proceeds to start the program running by first setting an operation timer, F102. The time duration can be selected so as to provide the most effective physical display of information; that is, the time setting should allow for an updated $SO_2$ or $O_2$ measurement that can be readily observed and yet would accommodate changes in the contents of the gas emissions generated by the combustible process. A time duration of between 30 seconds and 3 minutes could be selected as appropriate.

After the operational timer has begun, the program loop executes the operation of reading the EMF signal presented to the data I/O device 30, F103, such signal being representative of the amount of $O_2$ present in the gas emissions. The processor element 32 then utilizes this value to calculate the % of $SO_2$ present in the gas emissions based on the equation: $\%SO_2 = 20.95\% - \%O_2$, F104. It should be understood that this equation holds true for a sulfur burning operation such as is used in a paper processing plant where sulfuric acid is a desired ingredient and where the byproducts associated with such process are essentially, air which includes $O_2$ and $N_2$, and $SO_2$. Should other fuels of known compositions be utilized, the processor element 32 could be reprogrammed to perform the appropriate calculation, such operation being contemplated as falling within the scope of the present invention.

For combustible processes which burn fuels other than those of the elemental sulfur type, it would still be appropriate to employ the $SO_2$ determining arrangement of the present invention provided that a means for determining an amount of excess $O_2$ present in the gas emissions, were included. Another fuel of a known composition (i.e. $H_2S$) burning with an oxidizer of a known composition (i.e. air, $O_2$, air and $H_2O$, etc.) could be utilized in this circumstance. The excess $O_2$ measured by the solid electrolyte oxygen probe assembly 10 could then be made to infer the measurement of any of the flue gas constituents.

Having calculated the amount of $SO_2$ present, the program loop then proceeds to determine the value that is to be displayed, such function requiring a reading of the status of the display select switch, F105. It should be understood that this function is optional; that is, the program loop could be modified to provide a display automatically in a format which could include alternate displays of $SO_2$ and $O_2$ or could default to the display of the preferred reading with the other value being stored for future reference.

Function blocks F106 through F110 illustrate the decisional process performed by the program loop based on the reading of the display select switch. Of course, it should be realized that the function blocks F105 through F110 could be replaced by a single function block, F201, in the event that a dual display device were available. Following the display of the $SO_2$ and/or $O_2$ values, the program loop executes an operation whereby the actual readings are stored in a separate memory location 32a associated with the processor device. This separate storage function, F111, is utilized for record keeping purposes and provides a backup for verifying readings that have been cycled through the display operation. The length of time that such records will be kept is determined as a function of the operational timer setting, government regulatory requirements for the keeping of such records, as well as how much memory storage is available.

After such memory storage operation, the program loop then determines if the operational timer setting has expired such that the next reading and calculation could be performed.

Although the hereinabove described embodiment constitutes a preferred embodiment of the invention, it should be understood that modifications can be made thereto without departing from the scope of the invention as set forth in the appended claims.

We claim:

1. An arrangement for determining an amount of $SO_2$ present in gaseous emissions resulting from a combustible process utilizing a fuel of a known composition, said $SO_2$ determining arrangement comprising:

means for measuring an amount of excess oxygen present in such gaseous emissions;

means for producing an indication of such amount of $SO_2$ as a function of such oxygen measurement, said producing means determining such amount of $SO_2$ based on such combustible process having as the essential elements of such gaseous emissions, air and such amount of $SO_2$; and, means for displaying such indication of such amount of $SO_2$ in a selectively alternating relationship with a corresponding display of such amount of oxygen, said displaying means defaulting to a display of such $SO_2$ amount in the absence of a selection between such $SO_2$ and such oxygen amounts.

2. An arrangement for determining an amount of $SO_2$ as set forth in claim 1 wherein said fuel of a known composition is a fuel essentially composed of elemental sulfur.

3. An arrangement for determining an amount of $SO_2$ as set forth in claim 2 wherein said means for producing an indication of such amount of $SO_2$ includes a processor element having associated memory capabilities and programmed so as to solve the calculation:

$$\text{Percent } SO_2 = 20.95 - \text{Percent } O_2$$

4. An arrangement for determining an amount of $SO_2$ as set forth in claim 1 wherein said oxygen measuring means is an oxygen probe having disposed therein a solid electrolyte which provides sufficient oxygen ion conduction.

5. An arrangement for determining an amount of $SO_2$ as set forth in claim 4 wherein said solid electrolyte is constructed of zirconium oxide.

6. A method of determining an amount of a particular constituent of the flue gas emissions resulting from a combustible process utilizing a fuel of known composition, said constituent amount determining method comprising the steps of:

oxidizing such combustible process with a known composition;

measuring an amount of excess oxygen resulting from such combustible process;

determining a second measurement of such particular constituent as a function of such measurement of excess oxygen, such second measurement being based on such combustible process having as the essential elements making up such flue gas constituents, such amount of such particular constituent and such excess oxygen in a known proportion;

displaying such amount of such second measurement in a selectively alternating relationship with a corresponding display of such amount of excess oxygen; and defaulting to a display of such second measurement in the absence of a selection between such second measurement and such amount of excess oxygen.

7. A method of determining an amount of a particular constituent of the flue gas emissions as set forth in claim 6 further comprising the step of storing, for record keeping purposes, information relating to such second measurement and such amount of excess oxygen.

* * * * *